United States Patent [19]
Wellinghoff

[11] Patent Number: 5,360,609
[45] Date of Patent: Nov. 1, 1994

[54] CHLORINE DIOXIDE GENERATING POLYMER PACKAGING FILMS

[75] Inventor: Stephen T. Wellinghoff, San Antonio, Tex.

[73] Assignee: Southwest Research Institute, San Antonio, Tex.

[21] Appl. No.: 17,657

[22] Filed: Feb. 12, 1993

[51] Int. Cl.$^5$ .................. A01N 25/04; A61K 7/44; C08K 3/02
[52] U.S. Cl. .................. 514/772.3; 424/60; 424/405; 424/408; 424/409; 424/410; 424/412; 252/187.21; 252/187.23
[58] Field of Search .................. 424/60, 405, 408, 409, 424/410, 412; 252/187.21, 187.23; 524/796, 845, 846, 876; 525/421, 422, 435, 540, 928; 528/332, 335, 336, 342, 345, 350, 353, 363, 392, 422

[56] References Cited
U.S. PATENT DOCUMENTS 4,889,654 12/1989 Mason et al. .................. 252/100
4,891,216  1/1990 Kross et al. .................. 424/661
5,126,070  6/1992 Leifheit et al. .................. 252/187.21

Primary Examiner—Thurman K. Page
Assistant Examiner—Carlos Azpuru
Attorney, Agent, or Firm—Warren & Perez

[57] ABSTRACT

A process incorporating a chlorine dioxide generating compound such as sodium chlorite into a polymer or oligomer film is coated onto various substrates. Controlled release is accomplished by absorption of moisture from the environment. The chlorine dioxide so released acts as a biocide and a fumigant. The chlorite is dissolved into a hydrogen bonded phase containing a monomeric, or polymeric amide or a monomeric or polymeric alcohol. This hydrogen bonded phase is then mixed with an incompatible apolar phase consisting of anhydride containing such as polymers such as maleic anhydride copolymers with olefins, grafted maleic anhydride-polypropylene polymers. Chlorine dioxide is released by direct reaction of the anhydride or hydrolyzed anhydride with the chlorite anion across the phase boundary. Increasing the molecular weight of the phases, increasing the phase incompatibility and decreasing the concentration of anhydride will all decrease the chlorine dioxide release rate.

5 Claims, No Drawings

CHLORINE DIOXIDE GENERATING POLYMER PACKAGING FILMS

TECHNICAL FIELD OF THE INVENTION

The present invention relates generally to a composition for reducing bacterial and fungal growth and repelling insects, and more particularly to an ionomeric composition having biocidal or insect repelling releasing agent and method for making same.

BACKGROUND OF THE INVENTION

Chlorine Dioxide ("ClO$_2$") has been incorporated in polymer [JP 63,296,758, NOK Corp, 1988; CA 111 P120181s] and ceramic beads [JP 63,274,434, Enkler Busin.K. K., 1988; CA 111 P11975h], and in a calcium silicate wrapped in non-woven cloth [JP 57,168,977, Enkler Busin.K. K., 1982; CA 98 P77552]to be used as a deodorant. Food preservation is an application where a gel form is preferred [JP Patent, Diamaru Kogyo Kaishi, Ltd., 1982; CA 97 22409]. Chlorine dioxide generating gels have also been used as topical applications for disinfection [A. J. Kenyon, S. G. Hamilton and D. M. Douglas, Am.J.Vet. Res., 45(5), 1101 (1986)].

Most attempts to generate chlorine dioxide involve acidification (and or chlorination) of a aqueous solution of chlorite, acidification (and/or reduction) of chlorates ["Comprehensive Inorganic Chemistry, The Halogens", Vol 3, R. C. Brasted, D. Van Nostrand Co., New York, 1954, p134–142] or reduction of a chlorite solution with aldehydes [U.S. Pat. No. 2,323,594, Mathieson Alkali Works, 1943]. Typically the preparation involves mixing component A (gel with suspended NaClO$_2$) with component B (gel with lactic acid) immediately prior to use. α-hydroxy carboxylic acids (citric, tartaric, malic, glycolic) are especially useful for generating ClO$_2$ by the reaction:

$$H^+ + NaClO_2 \rightarrow HClO_2 + Na^+$$

$$5HClO_2 \rightarrow 4ClO_2 + HCl + 2H_2O \quad \quad 1)$$

[Ger. Offen. 2,817,942, H.Allinger, 1979; PCT Int. Appl. WO, J. Mason, 1988, CA 110 P98205h]. Alternatively, NaClO$_2$ and lactic acid have been separately encapsulated in polyvinyl alcohol and then mixed with water to generate ClO$_2$ [Can. 959,238, Chemical Generators, 1974]. Formulations involving sulfonic acids are also available [Europ. Pat. Appl. EP 287,074, Alcide Corp., 1987; CA 111 P45299f].

Another method for the production of chlorine dioxide employs acetic anhydride in the reaction:

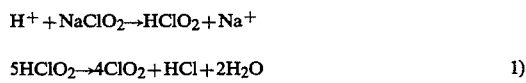

$$+ MeCOONa + O_2 \quad \quad 2)$$

(The unbalanced proton takes part in reaction 1) Interestingly prehydrolysis of the anhydride to acetic acid prior to the addition of chlorite produces no chlorine dioxide. Direct reaction of chlorite with anhydride in the presence of water is obviously important in the reaction [W. Masschelein, I and EC Prod. Res. and Dev., 6(2), 137 (1967)].

This work suggests the possibility of storing chlorite in a complex with an acid anhydride in a stable form until reaction with moisture liberates the chlorine dioxide [U.S. Pat. No. 2,482,134, R. Aston, 1949). Food packaging with the incorporated disinfectant, chlorine dioxide, brings up an important public health question pertinent to this practice: Does chronic ingestion of residual levels of disinfectants result in a significant genetic or carcinogenetic hazard to the human population. It is clear from published pharmacokinetic studies aided by incorporation of a chlorine radioisotope ($^{36}$Cl) that skin patch (Alcide gel) administration of chlorine dioxide and chlorite result in prolonged systemic residence of chlorine containing residues [J. Scatina, M. S. Abdel-Rahman, S. E. Gerges, Y. Khan and O. Gona, Fund.Appl.Tox., 4, 479 (1984)].

Meier et. al. published a report on the effect of subchronic and acute oral administration of chlorine, chlorine dioxide, sodium chlorite, and sodium chlorate on the induction of chromosomal aberrations and spermhead abnormalities in mice [J. R. Meier, R. J. Bull, J. A. Stober and M.C. Cimino, Environ. Mutagenesis, 7, 201 (1985)]. Only the highly reactive hypochlorite resulted in a weak positive effect for mutagenic potential. The disinfectants failed to induce any chromosomal aberrations or increased numbers of micronuclei in the bone marrow of mice. Other hazards which have been associated with chlorine dioxide but were not incorporated in the published study include hemolytic anemia and hypothyroidism. One of the reasons for the relatively innocuous effect of ClO$_2$ is its inability to produce halomethanes, unlike hypochlorite and chlorine [R. Vilagines et. al., Proc. AWWA Disinfect. Semin. 1977, paper 3, 24pp; CA 93 1735 13f].

In U.S. Pat. No. 4,585,482 has used the gradual hydrolysis of alternating poly (vinyl methyl ether-maleic arthydride) or poly (lactic-glycolic acid) to generate acid which can release chlorine dioxide from sodium chlorite. In the process a solution process is used to encapsulate a polyalcohol humectant and water with the polyanhydride or polyacid in a nylon coating. After sodium chlorite is permitted to diffuse into the capsule through the nylon wall, an impermeable polystyrene layer is coacervated around the nylon capsule. The capsules can be coated onto surfaces to release chlorine dioxide and provide biocidal action for several days to months.

Despite the many advantages of the '482 patent, there are some limitations. First, a large number of processing steps involving numerous chemical reactions and physical processes with disposal problems are required. Second, the chemistry is limited to batch processes. Third, a clear film cannot be produced. Finally, chlorine dioxide release starts immediately.

SUMMARY OF THE INVENTION

The object of the present invention is to improve over the prior art by a method which is continuous, safer and has minimal number of preparation steps.

The more specific objects of the invention are: to provide a low cost, chlorite containing oligomer or polymer that can be coated onto surfaces as a film prior to chlorine dioxide release. In addition, the invention provides a chlorite loaded film which will release chlorine dioxide over an extended period of time by exposure to moisture and both disinfect and repel insects from the surface onto which it is coated.

In the presence of water the local pH in the polymer film is reduced, releasing the chlorine dioxide.

The present invention disclosed herein comprises a method for making a composition which liberates a biocidal and/or insect repelling agent comprising the steps of dissolving a chlorite salt into a hydrogen bonded matrix to create a chlorite containing phase. The chlorite containing phase is then mixed with an incompatible phase having a hydrolyzable anhydride component therein to create a mixture having an ionomeric polymer. By exposing this mixture to the atmospheric moisture the ionomeric polymer liberates a chlorine dioxide compound to in effect act as a biocidal agent or an insect repelling agent.

In addition, the present invention discloses a composition which liberates a biocidal and/or insect repelling agent when exposed to a water source in accordance with the method of making as described above.

DETAILED DESCRIPTION

The preferred constituents of the apolar phase are styrene - maleic anhydride copolymers and their grafts with olefins. The monomers are cheap, commercially available and will form charge transfer complex that will polymerize thermally in the presence of small amounts of oxygen. Maleic anhydride contents between 0–50 mole % are available. At maleic anhydride concentrations below 33% the copolymers are soluble in apolar aromatic plasticizers.

In a preferred process equimolar amount of styrene-maleic anhydride monomer mix at 60° C. are added to a melt of plasticized, low molecular weight olefin such as, atactic polypropylene or other olefine in a Brabender Plasticorder equipped with a twin screw extruder. The styrene maleic-anhydride will spontaneously polymerize to a macroradical which will graft to the base polymer [N. Gaylord, ACS Adv. Chem. Ser., 129, 209 (1973); Z. Kopicova, J. Nemic and M. Protiva, Coll. Czechoslov. Chem. Commun. 41, 459 (1976)].

An alternative method to produce the desired anhydride substituted polymer is to copolymerize methacrylic anhydride with hydrophobic, aliphatic or aromatic vinyl monomers. Linear polymers that incorporate anhydride in the backbone generally require that the anhydride be included in mole percentages less than 6% [J.C.H. Hwa and L. Miller, J. Poly. Sci., 55, 197 (1961)].

The apolar phase may also contain components which may be induced to crosslink after film coating in order to stabilize the mechanical properties of the coating. These components include mixtures of hydrophobic epoxides and amines.

The gradual hydrolysis of the anhydride component in the presence of atmospheric moisture will generate acid functionality and ionomer formation. This will promote interphase compatiblization between the chlorite containing hydrogen bonded phase and the apolar phase containing the anhydride.

The preferred constituents of the hydrogen bonded phase include sodium chlorites or other chlorites where the cation may be an alkali, alkaline earth metal or transition metal ion or a protonatecl primary, secondary, tertiary amine or quaternary amine. The hydrogen bonded phase which solubilizes the chlorite can be monomeric or polymeric amides (e.g. formamide, isopropylacrylamide-acrylamide mixture) or monomeric or polymeric alcohols (e.g. methanol, 2-(2-ethoxyethanol). The amides are especially preferred since the amide functionality does not react with the anhydride below 150° C. In addition, chlorites, such as sodium chlorite remain stable in amides, such as formamide, up to 100° C.

The hydrogen bonded phase may also contain components which may be induced to polymerize after film coating in order to stabilize the mechanical properties of the coating. These components include hydrogen bonded epoxides and amines.

The final coating composition is made by mixing the hydrophobic and hydrogen bonded phases to the desired dispersion at temperatures below the decomposition temperature of the chlorite, preferably at temperatures less than 60° C. The coating is then applied as a hot melt to the substrate and then is induced to solidify by cooling to room temperature.

If both phases are mixed for short times at high viscosity little reaction of the anhydride with the chlorite occurs. However, if the dispersion is very fine, the phase compatibility very high (similar solubility parameters for the apolar phase and hydrogen bonded phase) and the viscosity of the phase is low extensive production of chlorine dioxide is observed even in dry films.

Exposure of the solid, unreacted film to water will hydrolyze the anhydride groups, compatiblize the phases and induce chlorine dioxide release. Thus chlorine dioxide release can be controlled by phase dispersion, phase viscosity, and exposure to atmospheric moisture.

The present invention is further illustrated by the following example.

A 7 wt% solution of sodium chlorite was made in 33w1% formamide:33wt% acrylamide:33wt% isopropylacrylamide (hydrogen bonded phase). Next a 40% solution of a 33mole%maleic anhydride:66-%moles styrene copolymer solution in ethylbenzene plasticizer (apolar phase) was vortex mixed with the hydrogen bonded, chlorite containing phase. The resultant white blend of the two disperse phases started a sustained release of chlorine dioxide in the absence of added water within five minutes at room temperature due to interphase diffusion and reaction.

The release rate could be slowed by cooling the mixture to 0° C. or by increasing the viscosity of the phases. Water was observed to hydrolyze the maleic anhydride to maleic acid and increase the rate of chlorine dioxide release.

While the preferred embodiments of the invention and their advantages have been disclosed in the above detailed description, the invention is not limited thereto but only by the spirit and scope of the appended claims.

What is claimed is:

1. A method for making a composition which liberates a repelling or biocidal agent which comprises the steps of:

dissolving a chlorite salt of a cation into hydrogen bonded matrices to create an amine containing phase; and mixing said amine containing phase with an incompatible phase having a hydrolyzable arthydride component therein to create a mixture having an ionomeric polymer; and exposing said mixture to atmospheric moisture at a temperature below which chlorine decomposes such that said ionomeric polymer releases chlorine dioxide when exposed to said atmospheric moisture in order to liberate a repelling or biocidal agent.

2. The method as recited in claim 1, wherein said chlorite cation comprises an alkali, alkaline earth, transition metal, protonated primary amine, protonated secondary amine, protonated tertiary amine, quaternary monomeric amine, quaternary polymeric amine or a mixture thereof.

3. The method as recited in claim 1, wherein said hydrogen bonded matrices comprises aliphates amides, aromatic antides, aliphatic alcohol, aromatic alcohol or a mixture thereof.

4. The method as recited in claim 1, wherein said hydrogen bonded matrices comprise formamide, acrylamide-isopropylacrylamide mixtures or their polymerized products, primary or secondary amines and their polymerization products with acrylamide, isopropylacrylamide and N,N methylene bisacrylamide and glycerine, ethylene glycol, or poly hydroxylic alcohols or mixtures thereof.

5. The method as recited in claim 1, further comprising the step of lowering the pH of said ionomeric polymer to less than 8.0.

* * * * *